(12) United States Patent
Gianomenico et al.

(10) Patent No.: US 6,413,953 B1
(45) Date of Patent: *Jul. 2, 2002

(54) PT(IV) ANTITUMOR AGENT

(75) Inventors: Christen M. Gianomenico, Blaine, WA (US); Ernest S. Y. Wong, Langley (CA)

(73) Assignee: AnorMED Inc. (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/679,952

(22) Filed: Oct. 4, 2000

Related U.S. Application Data

(63) Continuation-in-part of application No. 09/547,074, filed on Apr. 11, 2000

(60) Provisional application No. 60/128,939, filed on Apr. 13, 1999.

(51) Int. Cl.$^7$ .................... A61K 31/282; C07D 213/02; C07F 15/00; A61P 35/00

(52) U.S. Cl. ........................... 514/188; 546/2; 556/136; 556/137; 514/492

(58) Field of Search ............................ 546/2; 514/188

(56) References Cited

U.S. PATENT DOCUMENTS 5,194,645 A * 3/1993 Barnard ................. 556/137
5,665,771 A * 9/1997 Murrer ................... 514/492

* cited by examiner

*Primary Examiner*—Evelyn Mei Huang
(74) *Attorney, Agent, or Firm*—Morrison & Foerster LLP

(57) ABSTRACT

An improved platinum(IV) compound and its application as an antitumor agent are disclosed.

2 Claims, 1 Drawing Sheet cisplatin
(1 mg/ml)

cis-amminedichloro(2-methylpyridine)platinum(II)
(0.7 mg/ml)

compound A
(~80 mg/ml)

compound B
(~5 mg/ml)

compound C
(20 mg/ml)

compound D
(80 mg/ml)

compound E
(15 mg/ml)

compound F
(< 1 mg/ml)

compound G
(0.2 mg/ml)

PT(IV) ANTITUMOR AGENT

CROSS-REFERENCE TO RELATED APPLICATIONS

This application is a continuation-in-part of U.S. Ser. No. 09/547,074 filed Apr. 11, 2000, Provisional No. 60,128,939 Apr. 13, 1999 the contents of which are incorporated herein by reference.

TECHNICAL FIELD

The present invention relates to the area of platinum antitumor drugs. In particular, it relates to a specific platinum(IV) complex, and its application as an antitumor agent in the treatment of cancer.

BACKGROUND ART

Interest in platinum-based antitumor drugs has its origin in the discovery of the inhibitory effects of platinum complexes on cell division. Subsequent research and development led to the approval of the use of cisplatin, [$PtCl_2(NH_3)_2$] for cancer therapy. Cisplatin is now widely accepted and is one of the three most widely utilized antitumor drugs in the world. However, cisplatin has several disadvantages that include severe toxicity such as nephrotoxicity, neurotoxicity and emetogenesis. Cisplatin also has limited aqueous solubility (1 mg/ml) and is effective in a narrow range of tumors. Some tumors have natural resistance to platinum drugs while others develop resistance after the initial treatment.

In addition to cisplatin, carboplatin or diammine[1,1-cyclobutanedicarboxylato (2-)]-O,O'-platinum(II) has also received worldwide approval for use in cancer therapy. Carboplatin is less toxic than cisplatin and has greater aqueous solubility (14 mg/ml) but it is still only active in the same range of tumors as cisplatin. Many platinum complexes have been studied in an attempt to overcome the limitation of cisplatin (Wong, E.; et al., *Chem. Rev.* 1999, 9, 2451–2466).

A class of platinum compounds that has been reported to have activity against cancer is mixed amine platinum complexes of the general formula Pt(L)(L')$A_2$ or Pt(L)(L')$A_2B_2$ where L and L' are different amines, and where one of the amines sterically hinders access of Pt to the DNA of the tumor cell. One example within this class of compounds is cis-ammine(2-methylpyridine)dichloroplatinum(II) (Holford, J. F.; et al., *Anti-Cancer Drug Des.* 1998, 13, 1 and Raynaud, F. I., et al., *Clin. Cancer Res.* 1997, 3, 206–2074 and Holford, J. F., et al., *Br. J Cancer* 1999 77, 366 and U.S. Pat. No. 5,665,771). Other examples of antitumor compounds are bis-acetatoammine(cyclohexylamine)dichloroplatinum(IV) and bis-butyratoammine(cyclohexylamine)dichloroplatinum(IV) (Kelland, L. R.; et al., *Cancer Res.* 1992, 52, 3857; Kelland, L. R., et al., *Cancer Res.* 1992, 52, 822; Kelland, L. R.; et al., *Cancer Res.* 1993, 53, 2581 and U.S. Pat. No. 5,244,919.

The mixed amine platinum compounds have been reported to have antitumor activity in cisplatin resistant tumors. To compare the ability of various compounds to overcome platinum drug resistance, resistance factors are calculated for sets of cell lines. The resistance factor is defined as the ratio:

$$\frac{\text{activity against a parent line of cancer cells}}{\text{avtivity against a derivative of that cell line that has developed resistance to cisplatin}}$$

Thus, small resistance factors are preferred since the compound is better able to overcome the drug resistance of the cancer cells. The above cited compounds, Cis-ammine (2-methylpyridine)dichloroplatinum(II), bis-acetatoammine (cyclohexylamine)dichloroplatinum(IV) and bis-butyratoammine-(cyclohexylamine)dichloroplatinum(IV) were reported to have activity in certain cisplatin resistant tumors, but do not have equivalent activity in all cancer cells with different mechanisms of platinum drug resistance. For example, bis-acetatoammine(cyclohexylamine) dichloroplatinum(IV) and bis-butyratoammine(cyclohexylamine)dichloroplatinum(IV) have lower resistance factors in the set of 41M/41MR cancer cell lines than in the A2780/A2780R or CH1/CH1R sets of cells. On the other hand, cis-ammine(2-methylpyridine)dichloroplatinum(II) has a higher resistance factor in A2780/A2780R cell lines than in the 41M/41MR and CH1/CH1R cell lines. The platinum drug resistance in 41MR cells is due to reduced platinum accumulation, while in CH1R cells, the resistance is due to enhanced removal of and/or increased tolerance to Pt-DNA adducts. Resistance in A2780R cancer cells is due to detoxification via elevated glutathione levels, decreased uptake and increased DNA repair.

Despite the improved activity of these mixed amine platinum compounds compared to cisplatin in some platinum drug resistant cancer cells, their solubility in aqueous solution is limited; their aqueous solubility at ambient temperature and neutral pH are even lower than that of cisplatin. The limited aqueous solubility poses difficulties in the formulation and administration of these compounds. In particular, the iv administration of a platinum drug with low aqueous solubility may require the infusion of a large volume of liquid in order to achieve the therapeutic dose; a potentially long and inconvenient process.

Increasing the water solubility of platinum antitumor compounds has been an important practical objective of many platinum drug development programs. The solubility of cisplatin (~1 mg/ml,) approaches the practical limit of solubility for a cytoxic agent of its potency that is administered parenterally. Orally administered compounds can be less soluble, but they must be soluble enough to be absorbed. There is a desire to design platinum drugs with improved aqueous solubility as well as improved antitumor activity, particularly in cisplatin resistant tumors.

Citation of the above documents is not intended as an admission that any of the foregoing is pertinent prior art. All statements as to the date or representation as to the contents of these documents is based on the information available to the applicants and does not constitute any admission as to the correctness of the dates or contents of these documents. Further, all documents referred to throughout this application are incorporated in their entirety by reference herein.

DISCLOSURE OF THE INVENTION

The invention is directed to the platinum(IV) complex, ammine(chloro)trihydroxo(2-methylpyridine)platinum(IV), having the formula

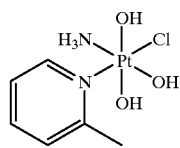

(hereinafter Compound A), and the pharmaceutically acceptable salts thereof, to pharmaceutical compositions thereof, and to methods to treat tumors using this compound.

Thus, a further aspect of the invention is Compound A for use in medicine and in particular for use in the treatment of cancer. A still further aspect of the invention relates to use of Compound A in the manufacture of a medicament for the treatment of cancer. Alternatively, there is provided a method of treating cancer comprising administering to a patient in need thereof, a pharmaceutically effective amount of Compound A, optionally along with additional medicaments.

MODES OF CARRYING OUT THE INVENTION

Aqueous solubility and antitumor activity, particularly against platinum resistant tumors are important objectives in the development of new platinum antitumor agents. Compound A has significantly improved aqueous solubility compared to the currently approved platinum drugs and compared to cis-amminedichloro(2-methylpyridine)platinum(II) and has greater or equivalent antitumor activity to cisplatin and to cis-amminedichloro(2-methylpyridine)platinum(II), particularly in resistant tumors. The latter finding is particularly unexpected as compounds B, C, D and E (FIG. 1) showed poorer activity. Platinum(IV) compounds in general are considered more inert than platinum(II) compounds and generally show lower antitumor activities than their platinum(II) analogs.

In in vivo studies in which the platinum compounds are administered at their maximum tolerated dose to CH1 tumor containing xenografts, a 32.8 days growth delay was achieved with Compound A, equivalent to the growth delay of 34 days achieved with cisplatin. This is in contrast to the growth delay of 0.6 days, achieved with compound E (FIG. 1).

Figure 1:
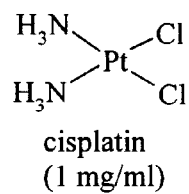
FIG. 1 shows structures of compounds A–G and of two additional Pt complexes.
Figure 1:
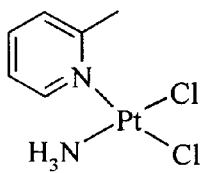
Figure 1:
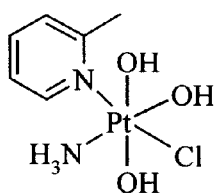
Figure 1:
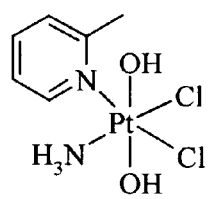
Figure 1:
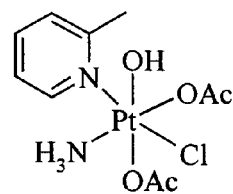
Figure 1:
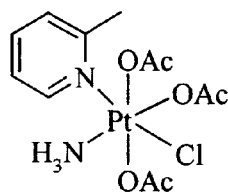
Figure 1:
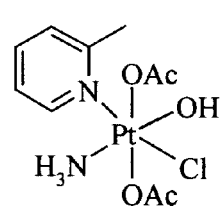
Figure 1:
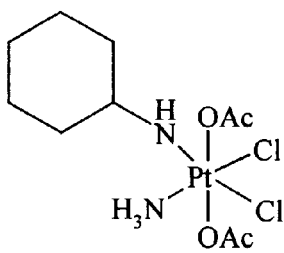
Figure 1:
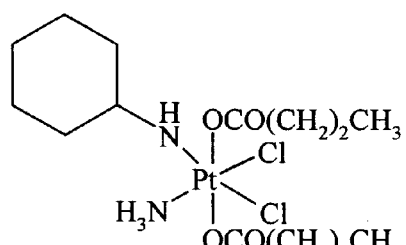

Compound A also exhibited significantly improved aqueous solubility compared to cisplatin, carboplatin, cis-amminedichloro(2-methylpyridine)platinum(II) and also some similar platinum(IV) compounds such as compound B, C, E, F and G (FIG. 1). The greater aqueous solubility of Compound A allows for an easier formulation and parental administration of the drug particularly the administration of the drug by intravenous infusion. A higher aqueous solubility would allow for a higher drug dose to be intravenously administered in a smaller volume of saline.

The combination of improved aqueous solubility and good antitumor activity makes Compound A an significant improvement over the current platinum drugs and over cis-amminedichloro(2methylpyridine)platinum(II) and sets it apart from other platinum(IV) compounds.

Compound A may be prepared by methods known in the art. General preparation methods for platinum complexes with mixed ammine/alkylamine ligands are given by Braddock, P. D.; et al., Chem.-Biol. Interactions 1975, 11, 145–161; and Giandomenico, C. M.; et al., Inorg. Chem. 1995, 34, 1015–1021.

One synthetic method is to react [PtCl$_3$(NH$_3$)]$^-$ with 2-methylpyridine to produce cis-amminedichloro(2-methylpyridine)platinum(II). [PtCl$_3$(NH$_3$)]$^-$ can be prepared from [PtCl$_4$]$^{2-}$ using methods known in the art (Giandomenico, Inorg. Chem. 1995, supra, and Abrams, J. J., et al., Inorg. Chim. Acta 1987 131, 3–4). Compound A can be generated from to cis-amminedichloro(2-methylpyridine)platinum(II) by reacting with hydrogen peroxide to produce amminedichlorodihydroxo(2-methylpyridine)platinum(IV), followed by reaction with hydroxide to produce Compound A. Another synthetic method is to prepare cis-amminedichloro(2-methylpyridine)platinum(II) from [PtCl$_4$]$^{2-}$ as starting material followed by reaction with hydrogen peroxide, followed by hydroxide to generate Compound A.

Compound A, including its salts, may be administered in the form of pharmaceutical compositions formulated according to well-known principles. Such compositions may be in the form of solutions of suspensions for injection, or to be in capsule, tablet, dragee, or other solid composition or as a solution or suspension for oral administration or formulated into pessaries or suppositories, or sustained release form of any of the above. Suitable diluents, carriers, excipients and other components are known. It may be desirable also to formulate a composition for topical administration such as an ointment or cream, or to be administered as a transdermal patch. Standard and well-known methods to formulate compounds similar to Compound A and compounds of this type in general are found in *Remington's Pharmaceutical Sciences*, latest edition, Mack Publishing Co., Easton, Pa.

The pharmaceutical compositions according to the invention may contain dosages determined in accordance with conventional pharmaceutical methods, suitably to provide active compounds in the dosage range in humans of from 0.1 to 100 mg/Kg body weight per day, in a single unit dose or in a number of smaller unit doses. Preferred dosage ranges are 1 to 30 mg/Kg body weight per day.

The dosage suitable for any particular subject is conveniently optimized by the ordinary practitioner. Individual dosages depend on the condition of the subject, the judgment of the practitioner, the severity of the condition, the mode of administration, and the manner of formulation. Optimization of individual dosages is routine and such individual dosages may fall outside the preferred ranges set forth above.

Compound A may be administered alone or in combination with another chemotherapeutic agents such as gemcitabine, etoposide or taxol, either as a single treatment or course of treatment or as part of combined therapy with other pharmaceuticals to overcome or diminish side effects or to improve bioavailability, or in combination with other therapies such as radiation treatment.

The following examples are for illustration, and are not intended to be limiting of the present invention.

EXAMPLE 1

Synthesis of Compound A
A. Synthesis of K[PtCl$_3$(2-picoline)]:
K$_2$[PtCl$_4$] was ground into a very fine powder with a mortar and pestle. 3.5047 g (8.443 mmoles) of K$_2$[PtCl$_4$] was placed in a 25 ml round bottom flask and 6–7 ml of dry NMP was added. 0.8648 g (9.286 mmoles) of 2-picoline was placed in 3–4 ml of NMP and divided in 5 equal portions. The first portion of 2-picoline was added to the Pt mixture. The mixture was completely immersed in a 60° C. oil bath and stirred at 1200 rpm. Subsequent portions of 2-picoline was added at 30–35 minutes internals. The rate of 2-picoline addition was 20% every 30–35 minutes. After the addition of the last portion, the reaction was allowed to proceed for another 50 to 60 minutes. The reaction solution was orange in color at the end of the reaction. The reaction solution was allowed to cool to ambient temperature. 100 ml of methylene chloride was added to the reaction at ambient temperature. The addition of methylene chloride caused the precipitation of K[PtCl$_3$(2-picoline)] and KCl. The precipitate was collected by vacuum filtration using a glass frit and washed with methylene chloride (3×5 ml), followed diethyl ether (3×5 ml). The precipitate was dried under vacuum at ambient temperature for 16–24 hours and weighed. Yield: 3.8440 g (86.8%). Anal. to Calcd (found) for $C_6H_7N_1Cl_3KPt.1.2 K_1Cl_1$: C, 13.74 (13.54); H, 1.35 (1.39); N, 2.67 (2.59); Cl, 28.51 (28.32). $^1$H NMR (300 MHz, DMF-d$^6$): 9.12 (d, 1 pyridine H); 7.90 (t, 1 pyridine H); 7.61 (d, 1 pyridine H); 7.40 (t, 1 pyridine H); 3.40 (s, 3 methyl H). $^{195}$Pt NMR (300 MHz, DMF-d$^6$): conforms to reference. HPLC retention time: conforms to reference.

B. Synthesis of cis-[PtCl$_2$(NH$_3$)(2-picoline)]:

6.819 g (12.50 mmoles) of K[PtCl$_3$(2-picoline)]. 1.5 KCl was placed in a 25 ml round bottom flask and 10 ml of 2.5 N KCl solution added. 8.2688 g (63.12 mmoles) of ammonium acetate trihydrate was dissolved in 25 ml of 2.5 N ammonium hydroxide solution and added to the stirring Pt mixture. The total volume of the reaction was ~35 ml. The orange colored mixture was immersed in a 45° C. oil bath and was stirred for 1 hour in the dark at >1000 rpm. The orange mixture gradually turned into a yellow colored mixture. The yellow precipitate was collected by vacuum filtration using a glass frit and washed with water (2×5 ml) and acetone (3×5 ml). The precipitate was dried under vacuum at ambient temperature for 16–24 hours and weighed. Yield: 3.8996 g (83%). Anal. Calcd (found) for $C_6H_{10}N_2Cl_2Pt$: C, 19.16 (19.25); H, 2.68 (2.72); N, 7.45 (7.43); Cl, 18.85 $^1$H NMR (300 MHz, DMF-d$^6$): 9.19 (d, 1 pyridine H); 8.03 (t, 1 pyridine H); 7.15 (d, 1 pyridine H); 7.51 (t, 1 pyridine H); 4.39 (bs, 3 NH$_3$ H); 3.34 (s, 3 methyl H). $^{195}$Pt NMR (300 MHz, DMF-d$^6$): conforms to reference. HPLC retention time: conforms to reference.

C. Synthesis of c,t,c-[PtCl$_2$(OH)$_2$(NH$_3$)(2-picoline)]:

5.0 ml of water and 5.0 ml 30% H$_2$O$_2$ was added to a suspension of 3.142 g of ZD0473 in 15–20 ml of heptane. This mixture was stirred and heated to ~80° C. for 2 hours. The mixture was cooled to room temperature and then stirred for 1 hour in an ice bath. The bright yellow solid was collected by vacuum filtration and washed with water and methanol. The product was dried under vacuum at ambient temperature overnight. Yield: 2.975 g (87%). Anal. Calcd (found) for $C_6H_{12}N_2Cl_2O_2Pt$: C, 17.57 (17.67); H, 2.95 (2.93); N 63 (6.79) Cl, 17.29 (17.39).

D. Synthesis of PtCl(OH)$_3$(NH$_3$)(2-picoline)] (Compound A):

0.246 g of LiOH.H$_2$O was dissolved in 5 ml of water. 2.402 g of c,t,c-[PtCl$_2$(OH)$_2$(NH$_3$) (2-picoline)] from paragraph C was suspended in this solution. The mixture was stirred overnight at ambient temperature. The yellow solid gradually dissolved overnight. The pH of the solution was adjusted to 7. The solvent was removed under reduced pressure to yield a yellow solid. In order to wash away the resulting LiCl, the solid was stirred in 10 ml of ethanol for 30 min. The mixture was centrifuged and the supernatant decanted off. This washing process was repeated until lithium chloride was removed. The product was dried under vacuum at ambient temperature overnight. Yield: 1.209 (50%). Anal. Calcd (found) for $C_6H_{13}N_2ClO_3Pt.2H_2O.0.12$ LiCl: C, 16.65 (16.45); H, 3.96 (4.04); N, (6.47 (6.75); Cl, 9.17 (9.47).

E. Alternative Synthesis of [PtCl(OH)$_3$NH$_3$)(2-picoline)] (Compound A):

3.83 g (0.0098 mol) of c,t,c-[PtCl$_2$(OH)$_2$(NH$_3$)(2-picoline)] from paragraph C was dissolved in 55.8 ml of H$_2$O (approx. 10 minutes to completely dissolve). LiOH.H$_2$O (1eq, 0.401 g , 0.0098 mol) was added to this solution. The solution was stirred for 18 hours at room temperature while protected from light. After 18 hours, the pH of the solution (which may be basic, eg ~pH 9) was adjusted to ~pH 7 using a small amount of 1M HCl. The solvent was removed on a roto-evaporator to give a yellow solid that was transferred to a centrifuge tube. Ethanol (20 ml) was added and the suspension was shaken vigorously for 10 minutes before centrifuging the solid until it settled to the bottom of the tube. The liquid was decanted and washing procedure was repeated. The solid was collected and dried under vacuum.

The solid [PtCl(OH)$_3$(NH$_3$)(2-picoline)] (2.7 g, 0.0069 mol) was gently heated in 6 ml of H$_2$O until it had fully dissolved (it was not necessary to heat to the boiling point). Once fully dissolved, the solution was allowed to stand at room temperature for 3 hours then cooled to ~4° C. and allowed to stand overnight. (If crystals do not form, induce crystallization by seeding, scratching or agitating.) The crystals were collected by filtration and dried under vacuum.

Yield of [PtCl(OH)$_3$(NH$_3$)(2-picoline)] was 2.4 g, 0.0061 mol. Anal. Calcd. (found) for $C_6H_{13}N_2ClO_3Pt$: C:18.40 (17.98); H:3.34(3.31); N:7.15(6.88); Cl:9.05(9.11)O:12.25 (12.37).

EXAMPLE 2

Solubility of Compound A

The aqueous solubility of Compound A and some other platinum complexes at ambient conditions is shown in Table 1.

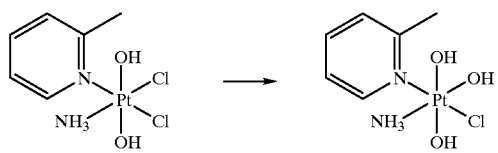

TABLE 1

| Compounds | Aqueous Solubility | Ratio to Solubility of cisplatin | Ratio to Solubility of cis-ammine(2-methylpyridine) Dichloroplatinum (II) | Ratio to Solubility of bis-butyrato-ammine-(cyclohexylamine) dichloro platinum (IV) |
|---|---|---|---|---|
| cisplatin | 1 mg/ml | 1 | 1.4 | 5 |
| carboplatin | 14 mg/ml | 14 | 20 | 70 |
| cis-ammine(2-methylpyridine) dichloroplatinum(II) | 0.7 mg/ml | 0.7 | 1 | 3.5 |
| Compound G (FIG. 1) | 0.2 mg/ml | 0.2 | 0.3 | 1 |
| Compound F (FIG. 1) | <1 mg/ml | <1 | <1.4 | <5 |
| Compound A (FIG. 1) | 80 mg/ml | 80 | 114.3 | 400 |
| Compound B (FIG. 1) | ~5 mg/ml | 5 | 7.1 | 25 |
| Compound C (FIG. 1) | 20 mg/ml | 20 | 28.6 | 100 |
| Compound D (FIG. 1) | 80 mg/ml | 80 | 114.3 | 400 |
| Compound E (FIG. 1) | 15 mg/ml | 15 | 21.4 | 75 |

As shown in Table 1, the solubility of Compound A is 80-fold that of cisplatin and significantly higher than the solubility of the other two listed prior art compounds. The only comparative compound solubility similar to that of Compound A is that of Compound D.

EXAMPLE 3

Anti Tumor Activity

Compounds were tested against human cancer cell lines grown in cell culture according to established procedures (described by Holford, et al., *British J. Cancer* 1998 77(3) 366–373). The results are shown below in Table 2. The results are given in concentrations ($\mu$M) necessary to achieve a 50% decrease in cell proliferation ($IC_{50}$), with resistance factors in brackets for the cisplatin-resistant cell lines. The cell lines bred to be resistant to cisplatin have the designation R, as in 41MR.

better than those of Compound D, the only compound compared to Compound A which has similar solubility characteristics.

EXAMPLE 4

Combined Solubility, Activity Comparisons

To determine the Pt(IV) compounds with the optimal aqueous solubility and antitumor activity, the Pt(TV) compounds (Compounds A–E) were compared with the Pt(II) analog, cis-amminedichloro(2-methylpyridine)platinum(II). For each of the Pt(IV) compounds, the ratio of Pt(IV) compound solubility over the Pt(II) compound solubility were calculated ($Sol_{Pt(IV)}/Sol_{Pt(II)}$). For each of the Pt(IV) compounds, the ratio of $IC_{50}$ of the Pt(IV) compound over the $IC_{50}$ of Pt(II) compound in various cell lines were calculated ($IC_{50-Pt(IV)}/IC_{50-Pt(II)}$). The mean ratio of ($Sol_{Pt(IV)}/Sol_{Pt(II)}$) over ($IC_{50-Pt(IV)}/IC_{50-Pt(II)}$) was then calculated for each compound. The larger the ratio of ($Sol_{Pt(IV)}/Sol_{Pt(II)}$) over ($IC_{50-Pt(IV)}/IC_{50-Pt(II)}$), the more optimal the

TABLE 2

| Compounds | 41M | 41MR | CH1 | CH1R | A2780 | 2780R |
|---|---|---|---|---|---|---|
| cisplatin | 0.26 | 1.2 | 0.11 | 0.71 | 0.33 | 5.2 |
|  |  | (4.6) |  | (6.5) |  | (15.7) |
| carboplatin | 3.3 | 8.8 | 1.3 | 6 | 1.8 | 25.9 |
|  |  | (2.7) |  | (4.5) |  | (14.4) |
| cis-ammine(2-methylpyridine)-dichloro platinum (II) | 5.6 | 6 | 2.2 | 2.1 | 2.5 | 12 |
|  |  | (1.1) |  | (1) |  | (4.8) |
| Compound F (FIG. 1) | 0.5 | 0.6 | 1.0 | 0.4 | 0.4 | 1.84 |
|  |  | (1.2) |  | (4) |  | (4.6) |
| Compound G (FIG. 1) | 0.072 | 0.048 | 0.0066 | 0.024 | NA | NA |
|  |  | (0.67) |  | (3.7) |  |  |
| Compound A (FIG. 1) | 25 | 45 | 6 | 12 | 9.5 | 41 |
|  |  | (1.8) |  | (2) |  | (4.3) |
| Compound B (FIG. 1) | 10 | 19 | 3.4 | 7.4 | 4.5 | 36 |
|  |  | (1.9) |  | (2.2) |  | (8) |
| Compound C (FIG. 1) | 27 | 26 | 8.6 | 17 | 8.6 | 45 |
|  |  | (0.96) |  | (1.8) |  | (5.2) |
| Compound D (FIG. 1) | >100 | >100 | 46 | 88 | 47 | >100 |
|  |  |  |  | (1.9) |  |  |
| Compound E (FIG. 1) | 78 | 78 | 18 | 46 | 10.5 | 62 |
|  |  | (1) |  | (2.6) |  | (5.9) |

As seen, Compound A has a resistance ratio comparable to that of known anti-tumor drugs. Of particular interest, however, is that its resistance ratio and $IC_{50}$ are dramatically compound. Compound A was found the have the most optimal aqueous solubility and antitumor activity of the Pt(IV) compounds listed.

|  | Compound A | Compound B | Compound C | Compound D | Compound E |
|---|---|---|---|---|---|
| $(Sol_{Pt(IV)}/Sol_{Pt(II)})$ | 114.3 | 7.1 | 28.6 | 114.3 | 21.4 |
| $(IC_{50\text{-}Pt(IV)}/IC_{50\text{-}Pt(II)})$ A2780 cell line | 3.8 | 1.8 | 3.4 | 18.8 | 4.2 |
| $(IC_{50\text{-}Pt(IV)}/IC_{50\text{-}Pt(II)})$ A2780R cell line | 3.4 | 3.0 | 3.8 | 8.3 | 5.2 |
| $(IC_{50\text{-}Pt(IV)}/IC_{50\text{-}Pt(II)})$ CH1 cell line | 2.7 | 1.5 | 3.9 | 20.9 | 8.2 |
| $(IC_{50\text{-}Pt(IV)}/IC_{50\text{-}Pt(II)})$ CH1R cell line | 5.7 | 3.5 | 8.1 | 41.9 | 21.9 |
| $(IC_{50\text{-}Pt(IV)}/IC_{50\text{-}Pt(II)})$ 41M cell line | 4.5 | 1.8 | 4.8 | 17.9 | 13.9 |
| $(IC_{50\text{-}Pt(IV)}/IC_{50\text{-}Pt(II)})$ 41MR cell line | 7.5 | 3.2 | 4.3 | 16.7 | 13 |
| mean ratio of $(Sol_{Pt(IV)}/Sol_{Pt(II)})$ over $(IC_{50\text{-}Pt(IV)}/IC_{50\text{-}Pt(II)})$ | 27.7 | 3.2 | 6.5 | 6.9 | 2.7 |

One having ordinary skill in the art to which this invention pertains in reviewing the specification and claims which follow would appreciate that there are equivalents to those claimed aspects of the invention. The inventors intend to encompass those equivalents within the reasonable scope of the claimed invention.

We claim:

1. A pharmaceutical composition comprising the compound ammine(chloro)trihydroxo(2-methylpyridine)platinum(IV), of the formula

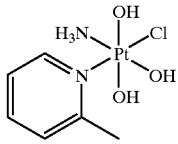

or a pharmaceutically acceptable salt thereof and a pharmaceutically acceptable carrier or diluent.

2. A method to treat ovarian cancer in a subject comprising administering to a subject in need thereof a pharmaceutically effective amount of the compound ammine(chloro)trihydroxo(2-methylpyridine)platinum(IV), of the formula

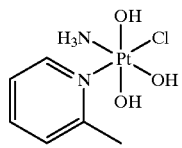

or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 6,413,953 B1 | Page 1 of 1 |
| DATED | : July 2, 2002 | |
| INVENTOR(S) | : Christen M. Giandomenico and Ernest S.Y. Wong | |

It is certified that error appears in the above-identified patent and that said Letters Patent is hereby corrected as shown below:

<u>Title page,</u>
Item [75], instead of "Gianomenico" the inventor's last name should read
-- Giandomenico --.

Signed and Sealed this

Thirty-first Day of December, 2002

JAMES E. ROGAN
*Director of the United States Patent and Trademark Office*